(12) United States Patent
Lu et al.

(10) Patent No.: US 6,776,039 B1
(45) Date of Patent: Aug. 17, 2004

(54) ALCOHOL CONTENT MEASURING INSTRUMENT

(76) Inventors: Shun-Tsung Lu, No. 112, Shiejung St., Shiecheng Village, Shin She Shiang, Taichung Hsien (TW); Ta-Wei Lu, 2719 E. Belmont Ciurt, Brea, CA (US) 92961

(*) Notice: Subject to any disclaimer, the term of this patent is extended or adjusted under 35 U.S.C. 154(b) by 0 days.

(21) Appl. No.: 10/358,233

(22) Filed: Feb. 5, 2003

(51) Int. Cl.$^7$ .................................................. G01N 9/00
(52) U.S. Cl. ............................ 73/444; 73/448; 73/451; 73/32 R; 215/365; 220/756
(58) Field of Search .................... 73/61.51, 305, 73/309, 426, 444, 448, 451, 32 R; D07/305, 533, 543, 536; 220/710.5, 771, 756; 215/396, 397, 365, 366; 116/228

(56) References Cited

U.S. PATENT DOCUMENTS

| | | | | |
|---|---|---|---|---|
| 111,885 A | * | 2/1871 | Tagliabue | ..................... 73/444 |
| 676,658 A | * | 6/1901 | Coffin | ......................... 139/168 |
| 745,521 A | * | 12/1903 | Redfearn | ....................... 73/444 |
| 1,249,565 A | * | 12/1917 | Wagner | ....................... 222/158 |
| 1,606,640 A | * | 11/1926 | Kaestner | ....................... 73/443 |
| 1,965,456 A | * | 7/1934 | Edelmann | ..................... 73/442 |
| 2,274,689 A | * | 3/1942 | Griffin | ......................... 73/444 |
| 2,616,287 A | * | 11/1952 | Nace | ............................ 73/448 |
| 2,713,258 A | * | 7/1955 | Walton | ......................... 73/448 |
| 4,077,265 A | * | 3/1978 | Strain | .......................... 73/445 |
| 5,447,248 A | * | 9/1995 | Rodriguez et al. | .......... 215/366 |

\* cited by examiner

*Primary Examiner*—Michael Cygan
(74) *Attorney, Agent, or Firm*—Rosenberg, Klein & Lee

(57) ABSTRACT

Disclosed herein is an alcohol content and temperature measuring instrument which is simply composed of a mug, an embolism an observation window, and a thermograph and a measuring tub. The measurement of alcohol concentration in a particular liquid can be measured according to Torricelli's law and Archimedes principle, while learn about the temperature of the liquid from the thermograph.

3 Claims, 3 Drawing Sheets

ALCOHOL CONTENT MEASURING INSTRUMENT

BACKGROUND OF THE INVENTION

1. Field of the Invention

The present invention relates to an alcohol content and temperature measuring instrument, in particular, to an alcohol content measuring instrument able to carry out measurement of concentration of alcohol in a particular liquid according to Torricelli's law and Archimedes principle.

2. Description of the Prior Art

Intoxication due to excessively drinking alcohol containing liquid hurts one's health severely, and often causes to do violence to other persons.

It is impossible for a person to know how much alcohol is contained in the liquor he/she is drinking or going to drink so as to prevent taking too much alcohol at a time. Therefore, it is very worth while to develop a simply constructed, efficiently and easily operatable yet inexpensive alcohol content measuring instrument.

Aiming at the above depicted problem, the present invention is to propose a newly developed alcohol content and temperature measuring instrument which have the above mentioned advantages through long time efforts of the present inventor.

SUMMARY OF THE INVENTION

One object of the present invention is to provide an alcohol content and temperature measuring instrument which is simply constructed, easily operatable yet inexpensive.

Another object of the present invention is to provide an alcohol content and temperature measuring instrument which carries out the measurement simply and accurately according to Torricelli's law and Archimedes principle.

Still another object of the present invention is to provide an alcohol content and temperature measuring instrument that is applicable to measure alcohol concentration in brewery.

Still another object of the present invention is to provide an alcohol content and temperature measuring instrument enables the user to learn about the temperature of the liquid inside the mug through a thermograph.

For achieving the above mentioned objects, the alcohol content measuring instrument of the present invention is composed of a mug in the form of a drinking cup; an observation bow window projected out of the mug and has at least one opening which is communicated with the mug and there is a circular exhausting hole beneath the observation bow window; a cone embolism whose outer diameter is placed inside the circular exhausting hole beneath the observation bow window; a measuring tube placed in the observation window; and a thermograph with graduation and is placed inside the observation bow window. The measuring tube is a sealed container having a series of uprightly marked graduations at the upper portion observable from the front, while a balancer weight is filled in its lower portion thereof. The mug and the observation window are fabricated in one piece.

In another embodiment, the observation window is formed within the mug.

With this structure, the alcohol concentration is measured according to Torricelli's law and Archimedes principle.

For fuller understanding of the nature and objects of the present invention, reference should be made to the following detailed description taken in conjunction with the accompanying drawings which are described below, while learn about the temperature of the liquid from the thermograph.

DETAILED DESCRIPTION OF THE PREFERRED EMBODIMENT

Figure 1:
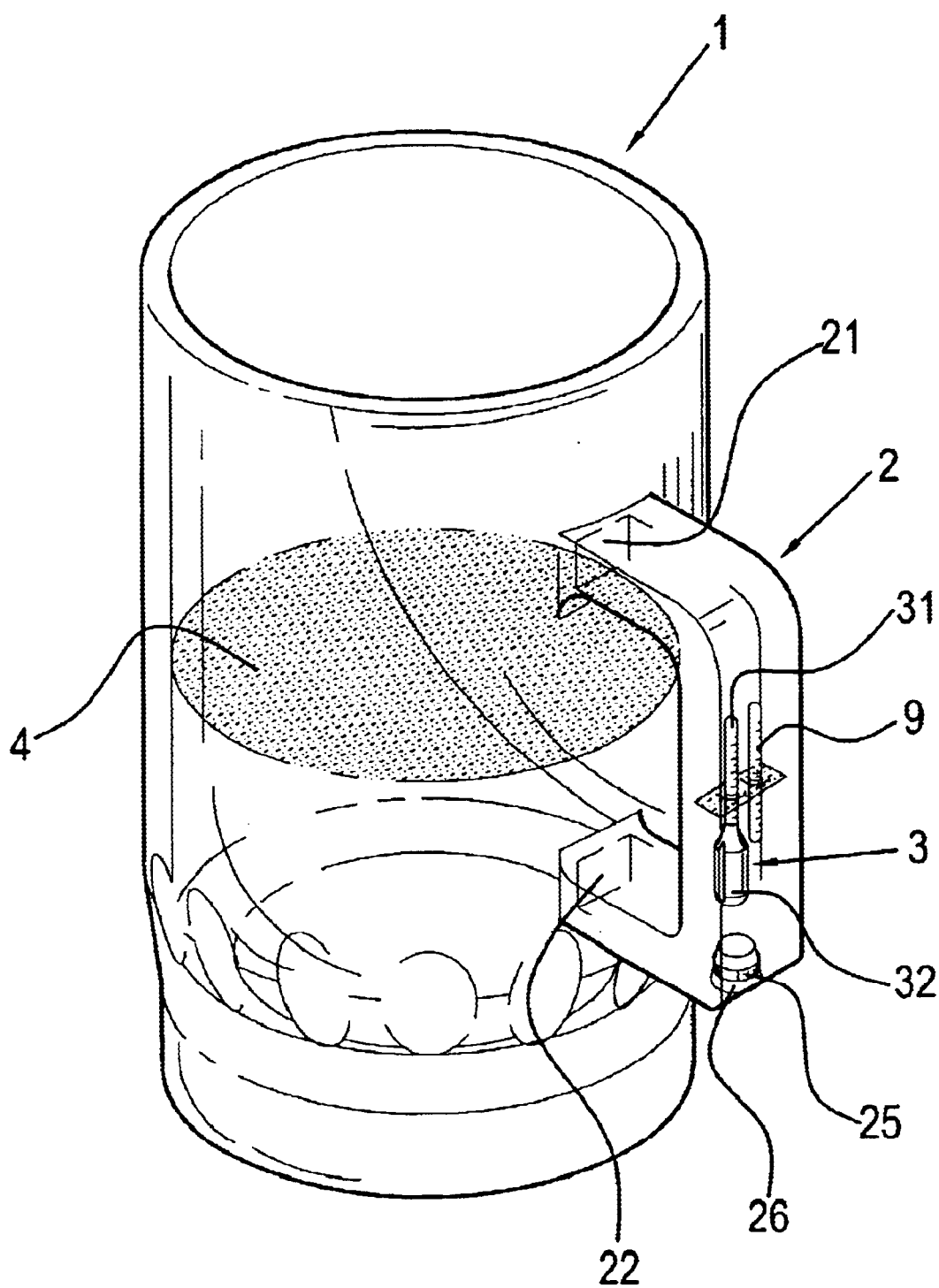
FIG. 1 is a three dimensional view of the alcohol content and temperature measuring instrument according to the present invention.
Figure 2:
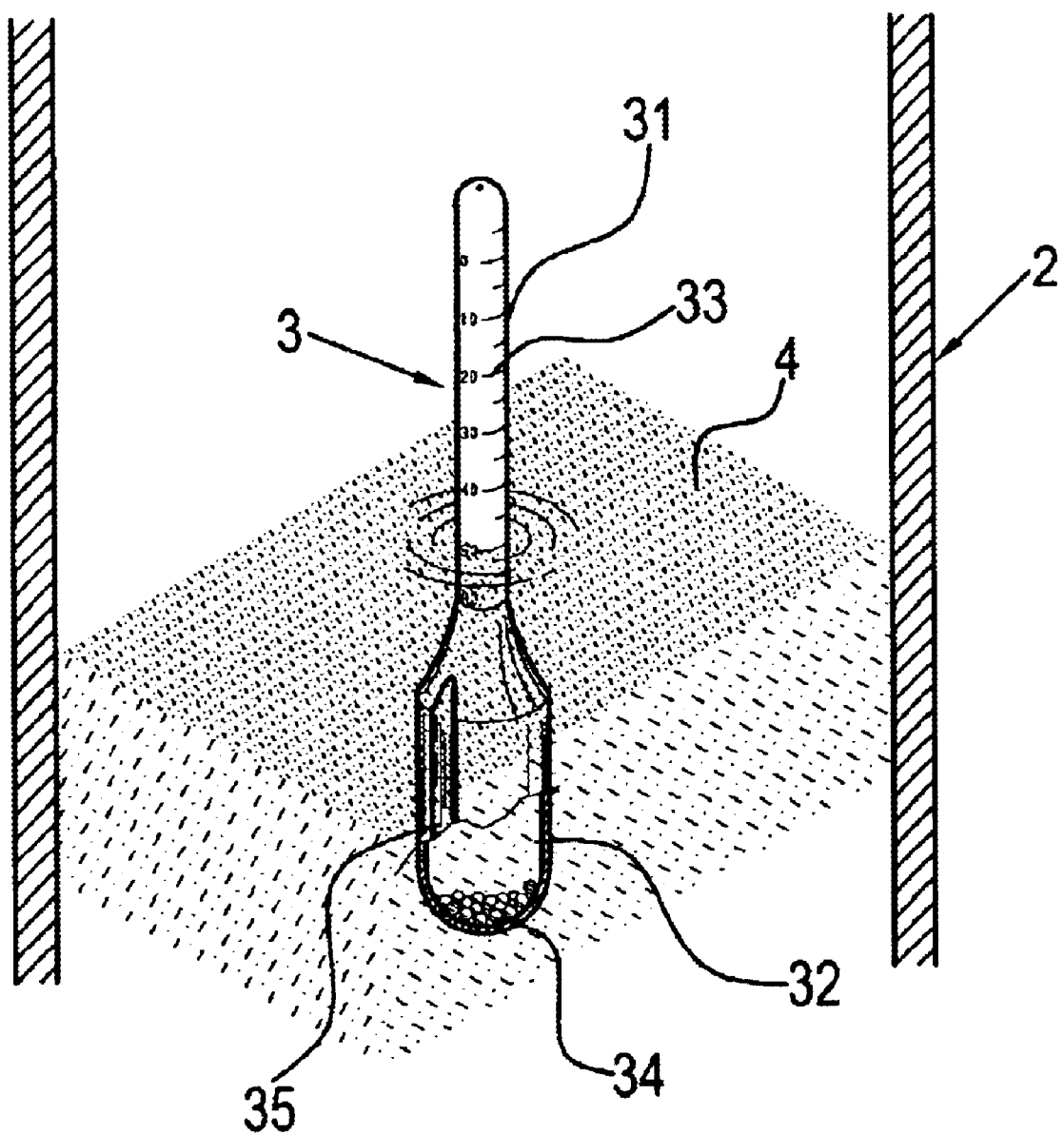
FIG. 2 is a perspective view of the measuring tube which is a component of the alcohol content and temperature measuring instrument according to a first embodiment of the present invention.

Referring to FIG. 1 together with FIG. 2, the alcohol content and temperature measuring instrument according to the present invention is essentially composed of a mug 1, an observation bow window 2, an embolism and a measuring tube 3 a thermograph 9. The observation bow window 2 is projected out of the mug 1 and has two openings 21 and 22 which are communicated with the mug 1 therefore the mug 1 and the observation bow window 2 are fabricated in one piece. The measuring tube 3 and the thermograph 9 are placed in the observation bow window 2, the measuring tube 3 is a scaled container having a series of uprightly marked graduations 33 (see FIG. 2) provided at the upper portion 31 thereof which can be observed from the front and a balancer 34 made of lead billets is filled in the lower portion 32 of the measuring tube 3. The type and shape of the balancer 34 is not specifically defined. The thermograph has graduation that measures the temperature of the liquid 4. Beneath the observation bow window 2 there is a circular exhausting hole 25 with an embolism 26 inside for blocking. The circular exhausting hole 25 is provided for cleaning the liquid 4 inside observation bow window 2.

The operational principle of the measuring instrument is as follows.

According to Torricelli's law, when an alcoholic, liquid such as wine or potable liquid is filled in the mug 1, the height of the liquid surfaces in the mug 1 and the observation bow window 2 is equal since the two vessels are communicated with each other. Then, according to Archimedes principle, the buoyancy force causing the upper portion 31 of the measuring tube 3 to float on the liquid surface is equal to the total weight of the measuring tube 3, that is the weight of the liquid expelled by the lower portion 32 of the tube 3 sinking beneath the liquid surface. From the above mentioned principle, it is understood that as long as the graduations 33 on the upper portion 31 of the measuring tube 3 are appropriately designed, the alcohol concentration of a liquid 4 can be easily and accurately reflected on the corresponding position on the graduations 33. The fillister 35 of the measuring tube 3 speeds up the balancing of the water pressure inside the observation bow window 2, thus speeds up the motion of the measuring tube 3 inside the observation bow window 2. The initialization zero position of the graduations 33 is obtained by filling the pure water (0% alcohol) in the instrument, and equipping the lower portion 32 with the balancer 34 made of lead billets of proper weight and a mark o representing the zero position is printed on the upper portion 31 of the measuring tube 3 where it contacts the water surface. Afterward the pure water is discarded and in similar way, a group of liquid with different alcohol concentration is successively filled in the mug 1 one after another without changing the balancer 34 so as to get a series of graduations 33 each corresponding to a particular alcohol concentration on the upper portion 31 of the measuring tube 3 thus completing the fabrication of the alcohol content measuring instrument of the present invention. It is well known that the specific weight of alcohol is approximately 0.8~0.9 at room temperature that is smaller than that of pure water (1), therefore, the greater the alcohol concentration is, the lower the measuring tube 3 descends, and the numerical value of graduations 33 increases upwardly along the measuring tube 3.

The circular exhausting hole 25 is placed beneath the observation bow window 2 whose embolism 26 inside the circular exhausting hole 25 can be removed for the discharge of the liquid 4 inside the observation bow window 2. When the liquid 4 is to be discharged from the circular exhausting hole 25, the fillister 35 on the measuring tube 3 balances the pressure inside the observation bow window 2, thus speeds up the discharge of the liquid 4 inside the observation bow window 2.

Figure 3A:
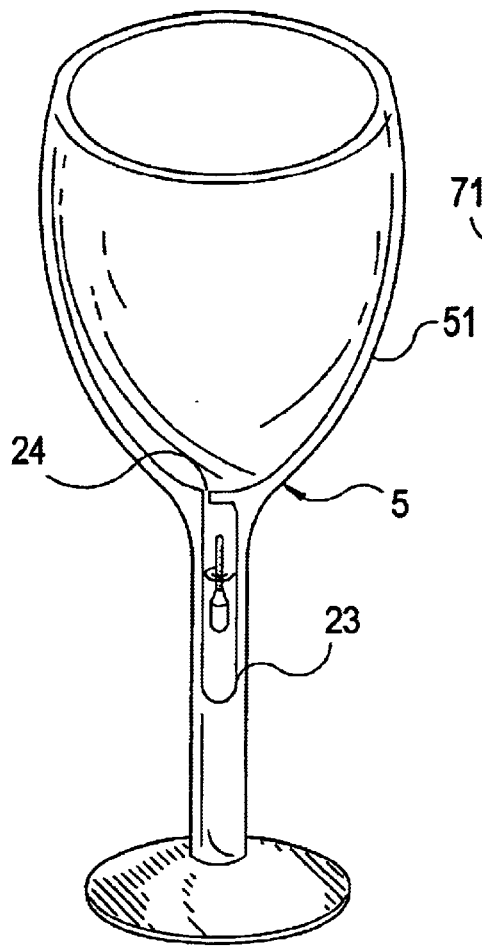
FIGS. 3A to 3C are perspective views of the alcohol content and temperature measuring instrument in second to fourth embodiments according to the present invention.
Figure 3B:
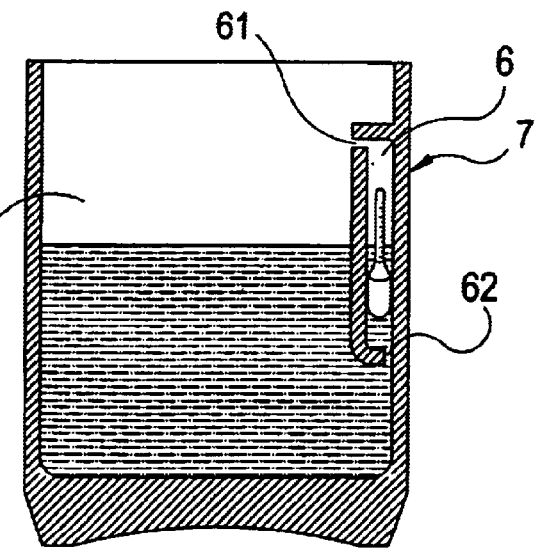
Figure 3C:
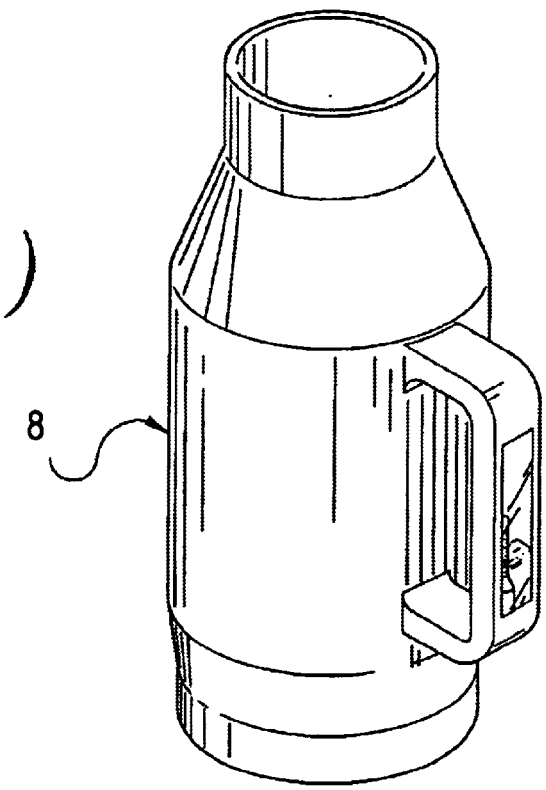

FIGS. 3A, 3B, and 3C are drawings which show second to fourth embodiments of the present invention respectively. In FIG. 3A, the observation window 23 has a single opening 24 provided for a goblet shaped container 51. In FIG. 3B, an observation window 6 is disposed in the inner space 71 of a cup 7 and has two openings 61 and 62. In FIG. 3C, the container 8 is formed into a medium sized pot 8 instead of the mug 1, or the goblet 5 or the cup 7 in other embodiments. As for the types of observation window, its opening, and measuring tube, all those combination described in the previous embodiments are compatible with the container 8 in fourth embodiment without affecting the structure or operating principle of the present invention.

It will be understood that the alcohol content and temperature measuring instrument in the present invention has several noteworthy advantage, in particular:

(1) The instrument is simply constructed, inexpensive, efficiently operatable with potential marketability.

(2) The instrument permits variety of different types.

(3) Materials for forming component parts are easily obtainable.

(4) The instrument is applicable both in commercial brewery and in school education for measuring alcohol concentration.

(5) Alcohol concentration based on various reference standards can be obtained by changing the balancer weight and graduation scale.

(6) No other test instrument is required to check the measurement results of the present invention.

While the present invention has been particularly shown and described with reference to particular embodiments thereof, it will be understood by those skilled in the art that various changes in forms and detail may be effected therein without departing from the spirit and scope of the invention as defined by the appended claims.

What is claimed is:

1. An alcohol content and temperature measuring instrument comprising:

a mug in the form of a drinking cup for accommodating a liquid for measuring its alcohol concentration;

an observation bow window projected out of said mug and having at least one opening communicated with said mug and a circular exhausting hole beneath said observation bow window; and a cone embolism whose outer diameter is placed inside said circular exhausting hole beneath said observation bow window;

a measuring tube placed in said observation bow window, said measuring tube is a sealed container having a series of uprightly marked graduations at the upper portion thereof observable from the front, while a balancer weight is filled in its lower portion thereof;

a thermograph with graduation and is placed inside said observation bow window.

2. The alcohol content and temperature measuring instrument of claim 1, wherein said observation window is formed within said mug.

3. The alcohol content and temperature measuring instrument of claim 1, wherein said mug and said observation window are fabricated in one piece.

* * * * *